United States Patent [19]

Kummer

[11] 4,260,263
[45] Apr. 7, 1981

[54] PROCESS AND APPARATUS FOR MEASURING THE BRIGHTNESS OF MILL-COMMINUTED PRODUCTS, ESPECIALLY FLOUR

[75] Inventor: Emanuel Kummer, Gossau, Switzerland

[73] Assignee: Gebrueder Buehler AG, Switzerland

[21] Appl. No.: 25,674

[22] Filed: Mar. 30, 1979

[30] Foreign Application Priority Data

Sep. 29, 1978 [CH] Switzerland ............... 10189/78

[51] Int. Cl.³ ........................................ G01N 21/55
[52] U.S. Cl. ................................ 356/448; 356/323; 356/425
[58] Field of Search ............ 356/448, 447, 408, 425, 356/323, 325, 434

[56] References Cited

U.S. PATENT DOCUMENTS

| | | | |
|---|---|---|---|
| 3,488,122 | 1/1970 | Roussopoulos | 356/408 |
| 3,684,378 | 8/1972 | Lord | 356/447 |
| 3,780,299 | 12/1973 | Bock | 356/448 |

FOREIGN PATENT DOCUMENTS

| | | | |
|---|---|---|---|
| 414205 | 12/1966 | Switzerland | 356/445 |
| 873563 | 7/1961 | United Kingdom | 356/447 |
| 1356049 | 6/1974 | United Kingdom | 356/448 |

OTHER PUBLICATIONS

IBM Tech. Disc. Bull., vol. 14, #6, (Nov. 1971), pp. 1868–1869.

Primary Examiner—Vincent P. McGraw
Attorney, Agent, or Firm—Larson, Taylor and Hinds

[57] ABSTRACT

Process and apparatus for measurement of brightness of milled products, especially flour, are disclosed. The process is of the general type in which the surface of a layer of flour is illuminated, and the returned quantity of light is taken to an optical electrical transducer. A light source is used for illumination, and the light beam is optically decomposed into at least two part-beams (reference beam and measurement beam) for transmission to the transducer. At least one of the part-beams is cyclicly interrupted or broken into two essentially time-shifted measurement phases in such a way that of the two part-beams, only one of the two-part beams will strike the transducer during a first measurement phase, and during a second measurement phase at least the other part-beam will be applied to the transducer. The output signals of the transducer are taken to a memory which intermediately stores the output signals of one measurement phase until the output signals of the following measurement phase appear, so that both output signals can be taken simultaneously to an evaluating device for determination of the relative brightness value of the measurement beam in comparison to the reference beam.

12 Claims, 8 Drawing Figures

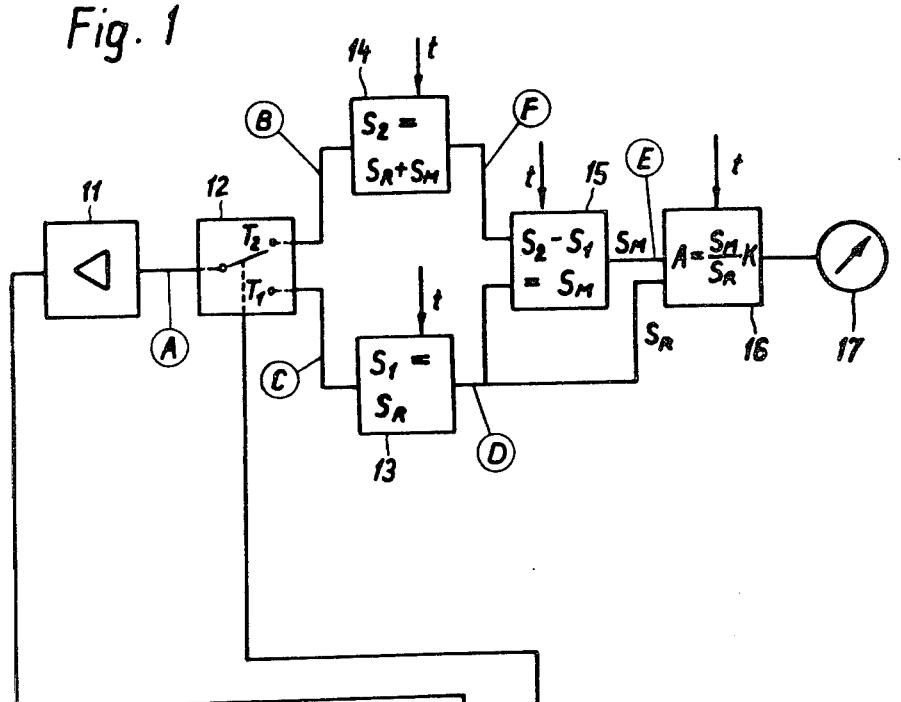
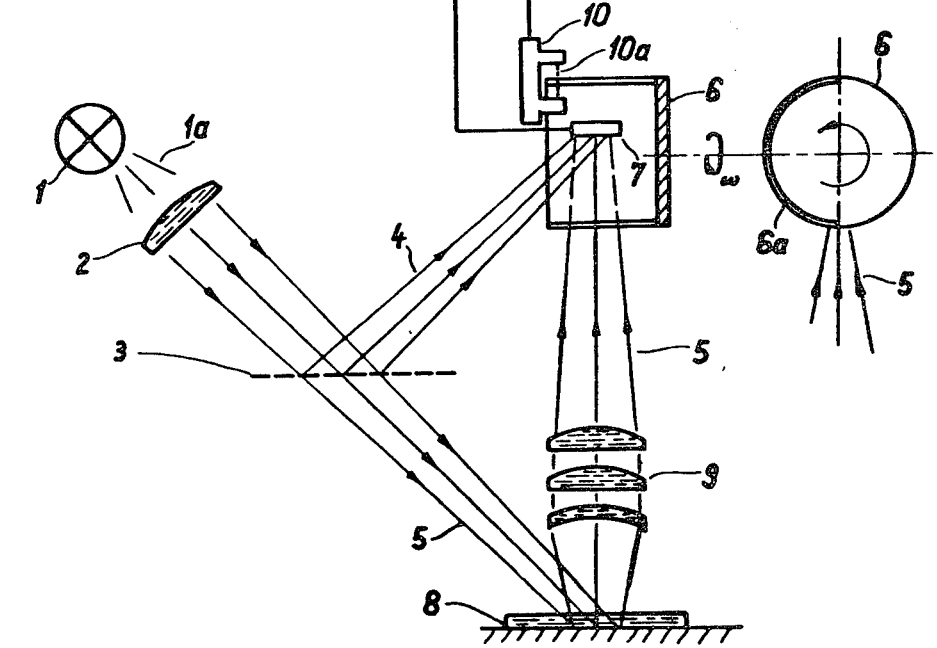
Fig. 1

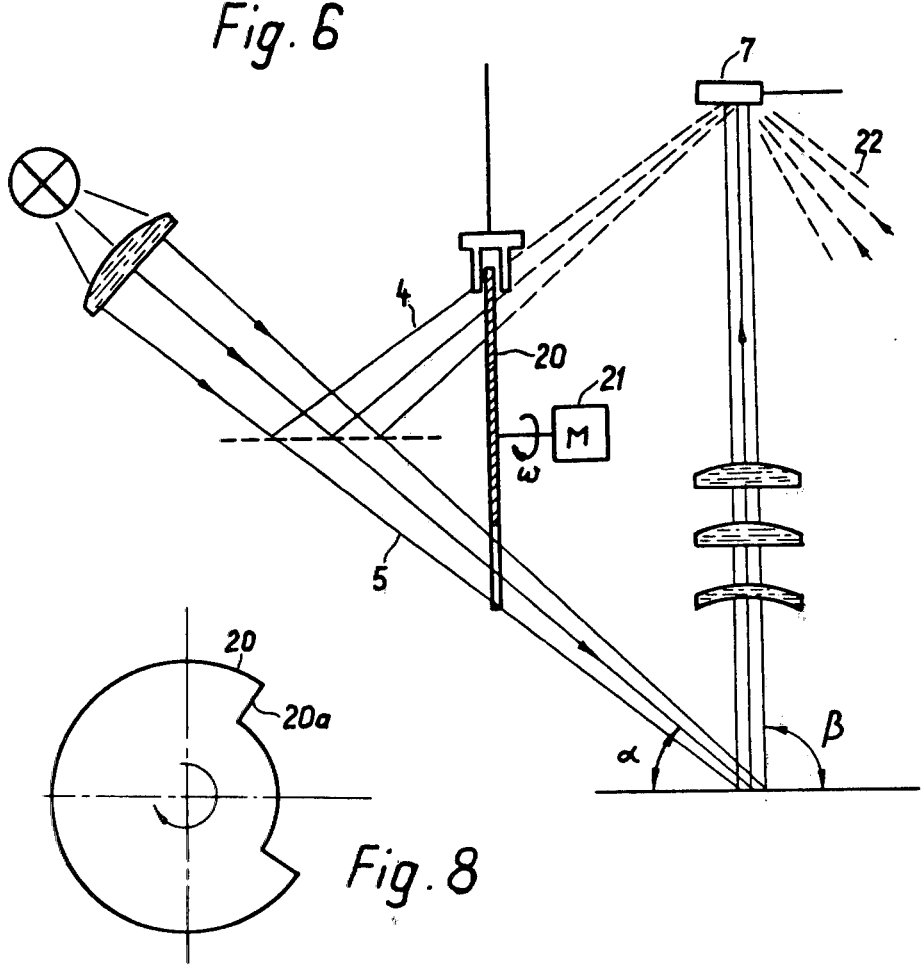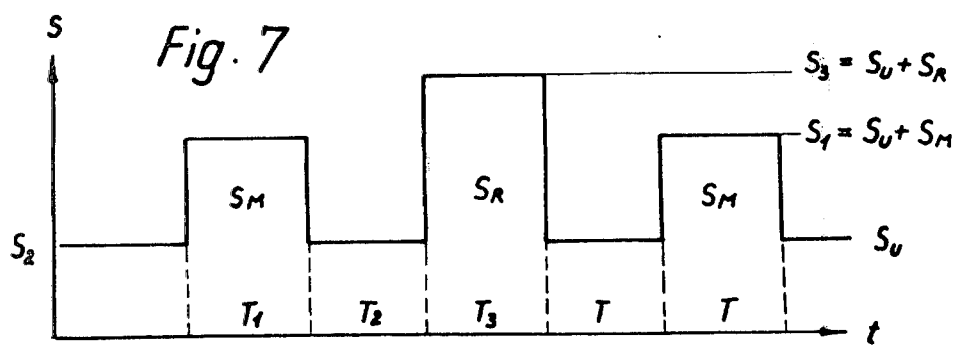

PROCESS AND APPARATUS FOR MEASURING THE BRIGHTNESS OF MILL-COMMINUTED PRODUCTS, ESPECIALLY FLOUR

FIELD OF THE INVENTION

This invention relates to a process and apparatus or devices for measurement of the brightness of mill-comminuted products, especially flour, particularly by means of a photosensitive element for conversion of light beams into electric signals, the process and apparatus being of the type wherein at least one light beam is split into at least a first part-beam and a second part-beam, wherein further the first part-beam (reference beam) is deflected to the photosensitive element for formation of a reference value, and the second part-beam (measurement beam) is deflected to the surface of a layer of flour for formation of the measurement value, and then is likewise deflected onto the photosensitive element, whereupon the electric output signals of the transducer, evoked by the reference beam and the measurement beam, are taken to an evaluating and indicating device, for determination of the brightness value of the measurement beam with respect to the reference beam.

BACKGROUND AND SUMMARY OF THE INVENTION

The objective in the production of flour is to produce the greatest possible yield of bright flours, i.e. white and dark flours on the one hand, and husks or bran which are free as possible of flour on the other hand. In practice these days, about 82% flour, whereof 60% is white flour, is sought from the milled wheat. Because of the complicated composition of grain and "mass" milling, a slight mixing of the fractions has to be accepted: particularly, dark flours contain husks, and bran contains flour.

The degree of intermixing directly affects the resulting flour brightness and is an important criterion of quality for the milled product. The price difference between bran and white flour is about 1:2, which results in the effort to get the most precise possible separation of the fractions, which can advantageously be monitored by control of flour brightness.

In the customary ash test for brightness, the husk parts give higher ash values by comparison to pure flours. The flour is bright or yellowish-white. The husk parts on the contrary are dark and impart a dark coloration to the flour. In the roundabout way of using ash, it can be determined how high the proportion of husk is in a flour sample, and from that in turn certain conclusions can be drawn as to the brightness of the flour. The time required, e.g. six or more hours, is a drawback in the ash test. For this reason, determination of the degree of brightness and the setting of the mill can only be retrospectively determined in the ash test. An immediate statement as to the momentary state of the product is not attainable with the ash test, so that it is not suitable for continuous monitoring or regulation of the mill.

The "Pekar test" therefore is generally used today for determining flour brightness. In this test, a control sample and a sample of flour that is to be tested are placed side-by-side on a spatula and the surface is smoothed and then the whole is moistened. Preparation is very simple and hardly takes a minute. The "Pekar test" allows an astonishingly fine determination of nuances of brightness, between the test sample and the control, with the naked eye.

There are brightness measuring instruments available on the market with which absolute values for brightness can be determined, within the scope of specific technical standards. Such brightness measuring instruments are an essential part of the manufacturing facility in many fields, e.g. the paper and textile industries, or in the production of coating materials, or in the dye industry.

Such instruments generally cannot be used suitably to measure the brightness of flour. This is explained particularly in that the majority of known measuring instruments and methods work with comparison of measured values of an optical electric measuring cell and an optical electrical comparison cell. These instruments are too inexact for precise testing. They have to be calibrated frequently, and they are unsuitable for continuous use, e.g. as control or regulating instruments. Swiss Pat. No. 414,205 shows such a known measurement method.

Another known reflecting instrument for determination of brightness presents a light source whose radiation is optically decomposed into two part-beams which then are converted by a modulator into intermittent light beams of different frequency. One of the modulated part-beams is taken directly to a photosensitive element and the other is deflected onto a colored surface that is to be tested, and the returned light is then also taken to the photosensitive element. This latter produces electric signals whose frequencies correspond to the frequencies of the two part-beams and whose amplitude is in proportion to the amplitude of the reference part-beam or of the reflected measurement part-beam. With use of frequency filtering devices, the measurement and reference signals are filtered out from the output signal of the photosensitive element and then, by difference formation or quotient formation, the amplitude of the measurement signal is determined in comparison to the amplitude of the reference signal, and therewith the relative brightness of the tested colored surface is established.

By use of a single light source for the measurement beam and the reference beam, as well as use of a single photosensitive element, obviously there is elimination of essential sources of error in known instruments. Thus, for example, a fluctuation of the brightness of the light source acts equally on the measurement beam and the reference beam, and this in turn is compensated in the comparison or in the quotient formation of the two output signals. The same is true of fluctuations due to aging of the photosensitive element, of voltage fluctuations, or of fluctuations in amplifier circuits that may be provided.

The disadvantage of this known reflecting measurement instrument resides particularly in that substantial technical problems and effort are involved in modulation of the light signals or the later separation of the two signal frequencies. This is because the precision of the result of measurement depends upon the precise separation of the two signal frequencies, with retention of the amplitudes that correspond to the light values. This involves use of expensive frequency filters. In addition, the known device is subject to disturbance because of the selected modulation method: clearly, each change in the rpm of the modulator plate leads to a change of frequency of the light or beams, which again can lead to errors of evaluation in the band filters or the frequency filters.

The invention relates to the problem of avoiding the drawbacks of the above-mentioned known devices, especially therefore to a method and device for brightness measurement of flour or other milled products, so that acceptable results will be obtained with simple construction, and the device can be utilized for brightness measurements in the laboratory and also especially for continuous brightness measurement in the field of quality control or regulation of a mill.

According to the invention, this is primarily achieved in that the beam path of the measurement beam is cyclicly broken into at least two essentially time-shifted measurement phases in such a way that of the two part-beams, during a first measurement phase, only the reference beam will strike the photosensitive element, and in that during a second measurement phase both the reference beam and the returned portion of the measurement beam will strike the photosensitive element, and at least one output signal of the photosensitive element will be intermediately stored during one measurement phase, and compared with at least one subsequent output signal of the other measurement phase.

Clearly, according to the invention there is no modulation of the light beams, but at least one of the part-beams is intermittently defleected or interrupted so that the other part-beam alone strikes the photosensitive element during at least one measurement phase. In this way there is no continuous "intermixing" of the two part-beams on the photoelectric transducer which would make elaborate separation and filtering necessary. Rather, by measurement of the output signals of the photosensitive element in the different measurement phases, a value can be obtained which is directly in proportion to the measured value or to the reference value. The structural outlay for the device can be kept particularly low if only one of the two part-beams is deflected or interrupted while the other part-beam falls continuously on the element.

There can be acceptable separation of the signals if the measurement beam and the reference beam are alternatingly deflected onto the photosensitive element. In this way many influences, e.g. from fluctuations of the light source or of the photosensitive element, are especially well compensated if for evaluation of the output signals the quotient is formed from the signal that corresponds to the brightness of the measurement beam and the signal that corresponds to the brightness of the reference beam.

The process of the invention can be embodied with particular simplicity in a measuring instrument which presents a deflector device for interruption of the beam path of at least one part-beam as well as a switching device connected at the output of the photosensitive element, one output of which switching device is connected to a first memory for intermediate storage of measurement value signals and whose second output is connected to a second memory for intermediate storage of the reference value signals, and which further presents a monitoring device that determines the respective first and second measurement phases, for control of the switching device. Clearly, it is hereby ensured that in the course of the process at least one of the part-beams will be applied uninfluenced by the second part-beam on the photosensitive element, and that besides the monitoring device will ensure an acceptable separation of the measurement phases so that the signal values in the two memories will be acceptably in proportion to the measurement value signals and the reference value signals respectively.

The monitoring device can be simply and reliably made if it is provided directly on the deflector device that effects the division of the part-beam/beams into the individual measurement phases. In practice an optical electrical monitoring device has been found to be especially useful, for monitoring the position of an aperture device, because in this way the control pulse for the monitoring device can be produced by the same aperture that effects the interruption of the measurement beam and/or the reference beam. In this way there is particularly good synchronizing of the measurement phases and the evaluation.

Insofar as control of the switching device is desired to be effected electronically, for separation of measurement value signals and reference value signals, threshold value measuring devices have proved their worth. These are connected to the output of the optical electrical transducer and control the switching device as a function of the amplitude of the signal appearing there.

The process of the invention can be effected with impinging of outside light, as well as without outside light. This can be managed with particular simplicity if the beam paths of the reference beam and the measurement beam are alternatingly interrupted in such a way that during one measurement phase only one of the part-beams and the outside light beam strike the photosensitive element, and during the second measurement phase at least the other part-beam and the outside light beam strike the photosensitive element, and in that during a third measurement phase both part-beams are interrupted so that only the beam of outside light will strike the photosensitive element, and in that at least one output signal of the photosensitive element will be intermediately stored during the first and second measurement phases and the signals compared with each other as well as at least one output signal during the third measurement phase. In this way the outside light, reference light and measurement light beams are advantageously separated, and by comparison or difference formation, the outside light can be eliminated and the relationship of the reference beam and the measurement beam can be determined. This is particularly advantageous for laboratory measurements in full ambient light.

However, the same process can be applied for continuous measurement or control of continuous production, and without any drawback the ambient light can be shielded or released by encapsulation of the measurement point with the measuring head. Obviously the process can be used for either application, whereby not least the liability to disturbance by outside light as a consequence of damage or wrong operation is reduced.

Since, in the task that is basic to the invention, namely the measurement of flour brightness, what is involved is one of the important control functions in the mill itself, and since further the brightness of the milled product is influenced e.g. by the setting of the roll frame, the cleaning, the preparation for grinding etc., there is regularly a certain range of scatter of brightness values. An additional part of the problem with which the invention is concerned is the elimination of the effect of the range of scatter, i.e. brief fluctuations of brightness, on the measured value. Advantageously, even before the formation of the quotient, the averages of the signals that correspond to the brightness of the measurement beam and the reference beam are determined over one or two or more measurement cycles. The result of the quotient formation is now advantageously indicated in percentages with reference to a standard, then recorded and examined for any exceeding or falling below specifiable limits. When the limits are exceeded, or the values go below the limits, an alarm can be tripped, or for example this variation can be incorporated in the operating process of the mill.

From the purely practical side of measured-value indication, it has proved to be advantageous that a result of quotient formation obtained in this way be indicated in percentages with respect to a standard as a line, and that the average value and the sensitivity of the drawing of the line be so selected that in normal operation of the mill there can be a straight line. A deviation of the registered quotients from a straight line can be signalled immediately as a deviation of the brightness of the product being measured. If the whole manufacturing process in the mill is precisely adjusted, the described representation of a line tracing or the straight line allows a positive assessment of the smooth running of the whole mill.

It also turns out to be advantageous to integrate the electric output signals of the photosensitive structural element of each individual phase during one or more periods of the network frequency. In this way the brightness of flour can be successfully measured and monitored, as required in practice in milling. All influencing factors and disturbance magnitudes are taken into consideration in the simplest way, e.g. fluctuations of the light source or of the photosensitive structure, temperature and outside light disturbances (ac or dc light).

Practically, the device for interruption of the beam path can be embodied especially simply and reliably if the deflector comprises a rotating drum that is disposed in the beam path of at least one part-beam, whereby the drum wall presents a window for cyclic release of the beam path, said window advantageously extending over about 180° of the drum periphery.

The invention thus allows, in the simplest way, the long-desired introduction of brightness measuring instruments in mills. Clearly, the technical advance and the inventive content of the subject of the application are ensured by the novel individual features as well particularly as by combination and sub-combination of the features that are utilized.

The invention is discussed below in example of embodiment, with reference to the drawings.

BRIEF DESCRIPTION OF THE DRAWINGS

FIG. 1 shows a schematic arrangement of a flour brightness measuring instrument with the features of the invention.

FIG. 6 shows a schematic arrangement of a modified measuring instrument with three measurement phases and impinging outside light.

FIG. 7 shows the signal characteristic at the output of the photosensitive element of the embodiment of FIG. 6.

FIG. 8 shows the aperture arrangement of the measuring instrument according to FIG. 6.

DESCRIPTION OF PREFERRED EMBODIMENTS

Figure 2:
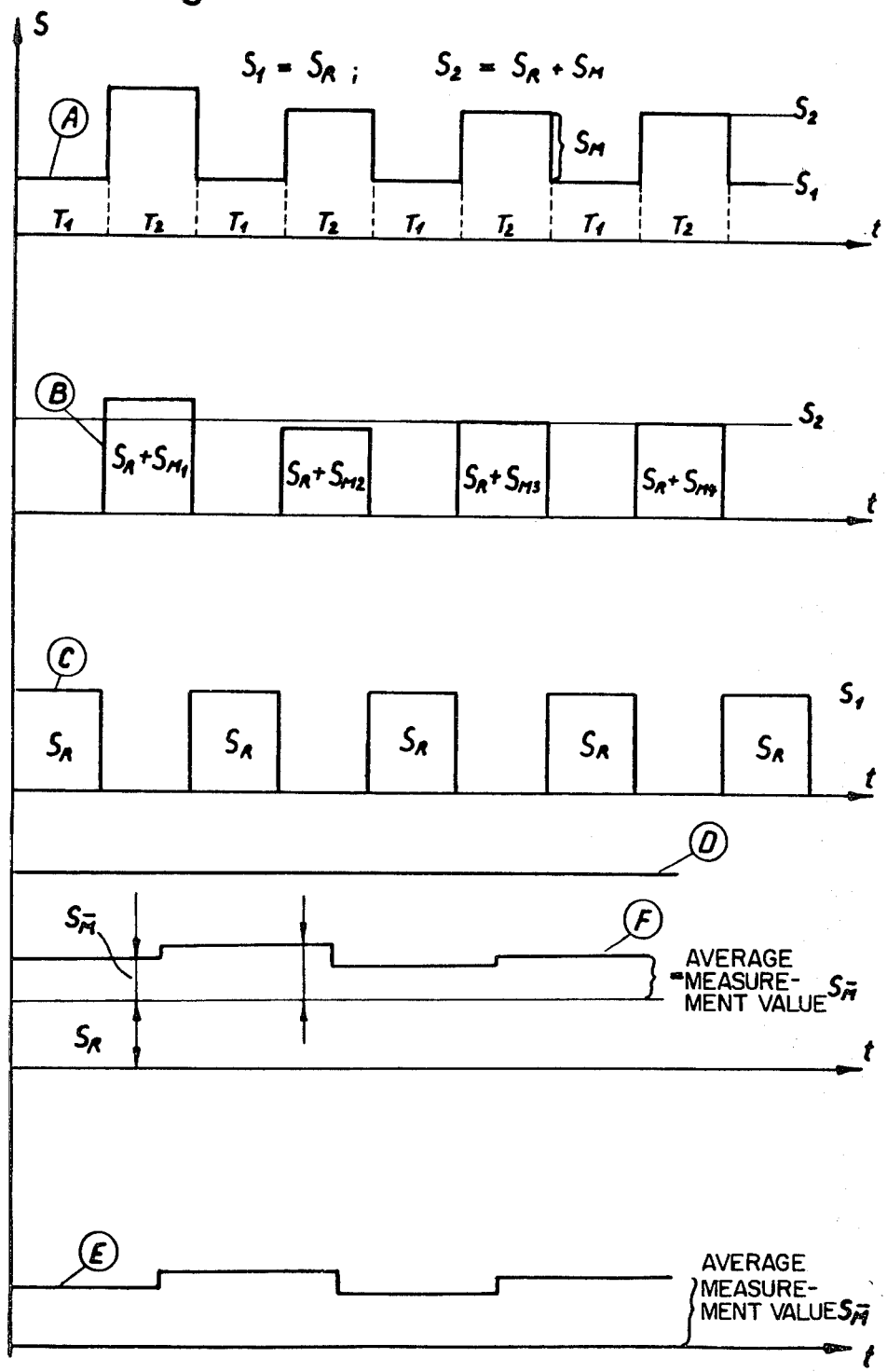
FIG. 2 shows the characteristics of signals at various points of the device according to FIG. 1.

According to FIG. 1, a flour brightness measuring instrument has a lamp 1 which produces a light beam 1a that is transmitted via a collecting lens 2 onto a semi-transparent mirror 3. Mirror 3 decomposes light beam 1a into two part-beams 4 and 5. Part-beam 4 is deflected directly onto a photocell 7 while part-beam 5 passes through mirror 3 and falls on a measuring surface 8 formed by a layer of flour that is covered by a glass plate. The light of part-beam 5 is returned from surface 8 as a function of the brightness value of the flour and is bundled by lens 9 and deflected onto photocell 7.

Photocell 7 is surrounded by a rotating drum 6 which has a cylindrical wall 6a on one peripheral side while the other peripheral side is left open. Depending upon the position of drum 6, which is driven by a drive that is not illustrated, the part of part-beam 5 collected by lens 9 is let through to photocell 7 or it is shielded by wall 6a. Whereas accordingly part-beam or reference beam 4 falls continuously on photocell 7, part-beam or mesuring beam 5 is cyclicly interrupted by drum 6. Structurally the device of drum 6 has proved to be especially simple, yet it is obvious that an interruption would be possible with use of other appropriate aperture devices or deflectors, to the extent that such devices would be disposed in the beam path downstream of mirror 3.

The input of an amplifier 11 is connected to the output of photocell 7, the output of said amplifier being connected to a switching device 12. The control input of switching device 12 is connected to a photoelectric monitoring device 10 which is provided staggered by 180° around drum 6 with reference to the light from lens 9. In the course of operation, therefore, drum wall 6a will always effect a switch control signal in monitoring device 10 when the beam path for the measurement beam 5 is opened from lens 9, and as soon as drum 6 has turned further by 180° and the beam path has again been interrupted, light path 10a of monitoring device 10 will again be open, and switch change control pulse will be sent to switching device 12.

The functioning of the device is discussed in connection with the signal diagram of FIG. 2. The signal diagram is intended only to show the characteristic of the signal without reference to the type (e.g. digital or analog) of signal, and without true fidelity to the amplitudes or curve and time characteristics.

During measurement phase $T_1$ measurement beam 5 is interrupted by drum wall 6a so that only reference beam 4 strikes photocell 7. Consequently, photocell 7 produces a signal that corresponds to reference beam 4, said signal being amplified in amplifier 11 and applied to the switching device. As soon as measurement beam 5 is released after a 180° turn of drum 6, the light impingement on photocell 7 is increased by a value that corresponds to the measurement beam, and is held over the whole duration of measurement phase $T_2$. After a further 180° turn the output value on photocell 7 drops again because drum wall 6a again enters the beam path of measurement beam 5. The curve characteristic at the input of switching device 12 is designated A in FIG. 2. Signal $S_1$ which is present during measurement phase $T_1$ accordingly corresponds to reference signal $S_R$ while the signal $S_2$ during measurement phase $T_2$ corresponds to reference signal $S_R$ plus measurement value signal $S_M$. The monitoring device 10 switches switching device 12 with phase $T_1$ to a first intermediate memory 13 and during the second measuring phase to a second intermediate memory 14. Signal D appears at the output of intermediate memory 13, said signal being obtained by memory 13 during the second measurement phase $T_2$, although signal $S_2$ has already appeared at the output of amplifier 11. During the same period, signal $S_2$ appears at the output of intermediate memory 14, so that in the second measurement phase $T_2$ signal $S_1$ and signal $S_2$ appear simultaneously at the input of computer circuit 15. In said circuit 15 the difference between signal $S_2$ and signal $S_1$ is formed, which of course allows production of measurement signal $S_M$ that is applied to the first input of evaluating circuit 16. The second input of circuit 16 is connected with the output of intermediate memory 13 so that reference signal $S_R$ appears there. In evaluation circuit 16, and indicator value A is formed in that measurement signal $S_M$ is divided by reference signal $S_R$ and the result is multiplied by an indicator constant K. The indicator constant derives from the kind of indication that is wanted, by an instrument 17, in a known way. Indicator value A is thus in every case in proportion to the quotient of the light value of reference beam 4 and measurement beam 5. Any brightness fluctuations of lamp 1 or fluctuations in sensitivity of photocell 7 are eliminated by the quotient formation. For reset, or for energizing individual elements, especially intermediate memories 13 and 14, computer circuit 15 and the evaluation circuit 16, the said elements may be connected with a synchronizing and control circuit that is not illustrated, which after completion of the individual mesurement phases $T_1$ and $T_2$ respectively will energize the elements in question or set them back to zero, to introduce a new measurement phase. The arrangement and selection of these structural elements is known to the specialist and in current use so that we will not describe them in detail.

Figure 3:
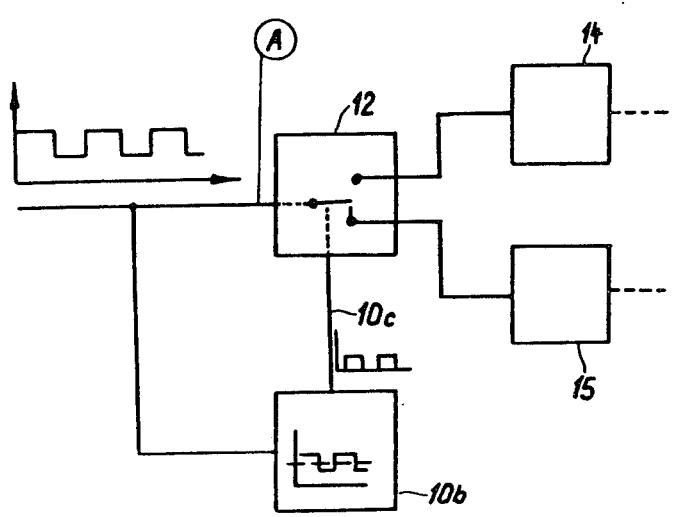
FIG. 3 illustrates a modification of the monitoring device according to FIG. 1.

FIG. 3 shows a somewhat modified example of embodiment in which there is provision of a monitoring device 10b. This is directly connected to the input of switching device 12 so that it also receives signals $S_1$ and $S_2$ (FIG. 2). Monitoring device 10b has a known threshold measuring device whose threshold value is so set that when an input signal is applied that exceeds value $S_R$, a signal is given to control lead 10c which in turn is connected with the control input of switching device 12. Consequently, switching device 12 is switched every time, as soon as the signal value at the input of monitoring device 10b rises when there is a shift from measurement phase $T_1$ to measurement phase $T_2$. In this way a photoelectric monitoring of drum 6 as in FIG. 1 can be eliminated. Otherwise the functioning of the device is identical with that of the example of FIG. 1.

Figure 4:
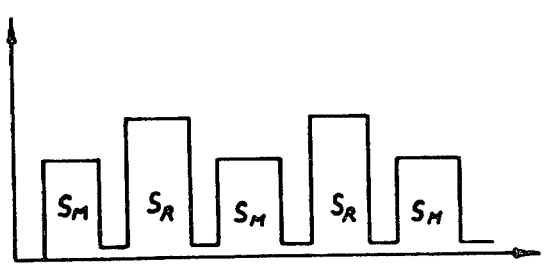
FIG. 4 is a modified curve of the output signals of the photosensitive element according to the embodiment of FIG. 5.
Figure 5:
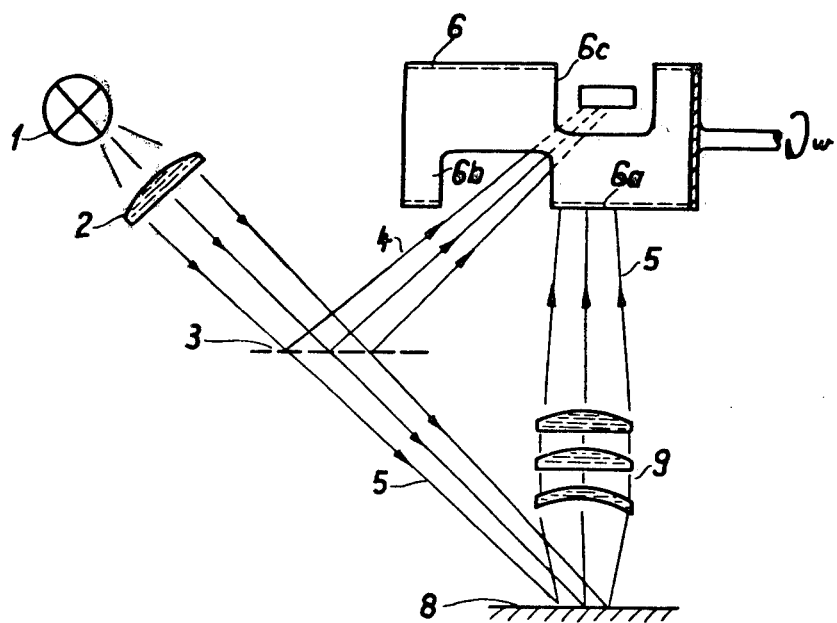
FIG. 5 shows a modified embodiment of the drum aperture of FIG. 1.

FIG. 4 shows the schematic signal characteristic of signals $S_M$ and $S_R$ in a modified arrangement of drum 6 according to FIG. 5. According to FIG. 5, drum 6 has two windows 6b and 6c, staggered by about 180° on the periphery of the drum. If drum 6 rotates, as in operation of the arrangement according to FIG. 1, reference beam 4 will be alternatingly released and measurement beam 5 interrupted, or reference beam 4 will be interrupted and measurement beam 5 released. Consequently there will be a signal characteristic $S_M$ and $S_R$ as in FIG. 4, where measurement value $S_M$ is presented directly, without difference formation. Consequently computer circuit 15 (FIG. 1) can be omitted in the evaluation circuit. Instead of the drum apertures shown in the examples, there can of course be plate devices or any other shielding devices or intermittent deflecting mirrors without going beyond the scope of the present invention. Also, arrangement of the circuitry is currently known to the specialist, and therefore various modifications of the structural elements can be adapted without exceeding the scope of the present invention.

FIG. 6 shows a measurement instrument according to FIG. 1, where instead of drum 6 a shutter plate 20 is provided, driven by a motor 21. As FIG. 8 shows, shutter plate 20 has a segment-like notch 20a, amounting to about 90°. Shutter plate 20 therefore cyclicly interrupts both measurement beam 5 and reference beam 4. This divides the measurement into three phases. In the setting according to FIG. 6 only the measurement beam 5 strikes photocell 7. As soon as plate 20 has turned further, measurement beam 5 is interrupted without immediate release of reference beam 4. In this phase outside (ambient) light indicated schematically by numeral 22 falls on photocell 7. In the next phase reference beam 4 is released while mesurement beam 5 is still interrupted. The signal characteristic at the output of photocell 7 is to be seen in FIG. 7. So long as both part-beams 4 and 5 are interrupted, only signal $S_U$ is delivered. As soon as part-beam 5 is released, measurement signal $S_M$ is added to signal $S_U$. In the next measurement phase part-beam 4 is released, so that the output signal rises to the value $S_U$ plus $S_R$. There are therefore three different values for the individual measurement phases, in proportion to the ambient light, the reference light and the measurement light. Since only the portion of the ambient light is present when both part-beams are cut off, by comparison or by substraction in mesurement phases T and $T_3$, there can be determination of the value of reference signals $S_R$ or measurement signals $S_M$. The circuit is operational of course even if there is no impinging of outside light, because only the base value of curve $S_2$ is affected by the outside light. The circuit therefore is especially reliable and opens a further field of possible practical applications.

Having thus described preferred embodiments of my invention, I claim:

1. In a process for measurement of the brightness of comminuted products from a mill, especially flour, by means of a photosensitive element for conversion of light beams into electric signals, wherein at least one light beam is split into at least a first part-beam comprising a reference beam and a second part-beam comprising a measurement beam, the reference beam is directed onto the photosensitive element for formation of a reference value, and the measurement beam is directed onto the surface of a layer of product to form a measured value, and the returned portion of the measurement beam is also directed onto the photosensitive element, whereupon the electric output signals of the photosensitive element evoked by the reference beam and the measurement beam are passed to an evaluating and indicating device for determination of the relative brightness value of the measurement beam in comparison to the reference beam reaching the photosensitive element, the improvement wherein the beam path of the measurement beam is cyclicly broken into at least two essentially time-shifted measurement phases such that only the reference beam of the two part-beams strikes the photosensitive element during a first measurement phase, and such that during a second measurement phase both the reference beam and the returned portion of the measurement beam strike the photosensitive element, and at least one output signal of the photosensitive element during one measurement phase is intermediately stored and is compared with at least one subsequent output signal of the other measurement phase.

2. Process as claimed in claim 1, wherein a quotient is formed from a signal of the photosensitive element that corresponds to the brightness of the measurement beam and a signal of the photosensitive element that corresponds to the brightness of the reference beam.

3. Process as claimed in claim 1, wherein the measurement beam is cyclicly broken before it encounters the surface of the layer of product.

4. Process as claimed in claim 1, wherein ambient light is shielded with respect to the photosensitive structure.

5. Process as claimed in claim 2, wherein the result of the quotient formation in percentage with reference to a standard normal value is recorded, and examined for exceeding or going below determined limits.

6. Process as claimed in claim 5, wherein the result of the quotient formation in percentage with reference to a standard normal value is presented as a line.

7. Apparatus for measuring the brightness of comminuted products from a mill, especially flour, comprising a light source, means for splitting a beam from said light source into a first part-beam comprising a reference beam and a second part-beam comprising a measurement beam, a photosensitive element for conversion of light beams into electric signals, means for directing the reference beam onto the photosensitive element for formation of a reference value, means for directing the measurement beam onto the surface of a layer of product and thence onto said photosensitive element to form a measurement value, a deflector for cyclicly breaking the beam path of the measurement beam into at least two time-shifted measurement phases such that only the reference beam of the two part-beams strikes the photosensitive element during a first measurement phase and such that during a second measurement phase both the reference beam and the measurement beam from the product surface strike the photosensitive element, means for temporarily storing at least one output signal of the photosensitive element during one of the measurement phases for comparison with at least one subsequent output signal of the other measurement phase, and means for receiving electrical output signals of the photosensitive element and determining the relative brightness value of the measurement beam in comparison to the reference beam reaching the photosensitive element.

8. Apparatus as claimed in claim 7 comprising a switch device connected at the output of the photosensitive element and having a first switch output connected to a first memory for intermediate storage of measurement value signals and a second switch output connected to a second memory for intermediate storage of reference value signals, and a monitoring device for determining respectively the first and second measurement phases and controlling said switch device.

9. Apparatus as claimed in claim 8, wherein the monitoring device is provided for determination of the actual operational setting of the deflector device.

10. Appratus as claimed in claim 9, wherein said deflector device comprises a rotating orifice device in the beam path of the measurement beam, and said monitoring device comprises an optical-electrical monitoring device to monitor the position of the orifice device, the output of the monitoring device being connected to the control input of the switching device.

11. apparatus as claimed in claim 8, wherein the monitoring device has a threshold measuring device connected with the output of the photosensitive element in such a way that the drop and/or rise of the signal at the output of the photosensitive element can be determined upon interruption of the beam path of a part-beam.

12. Apparatus as claimed in claim 8, wherein the deflector device comprises a rotary drum that is disposed in the beam path of at least the measurement beam, whereby the drum wall, for cyclical opening of the beam path, presents at least one window which extends over about 180° of the drum periphery.

* * * * *